May 10, 1949. E. HEMMING Plant Pat. 835
HYBRID MALLOW PLANT
Filed Aug. 27, 1947
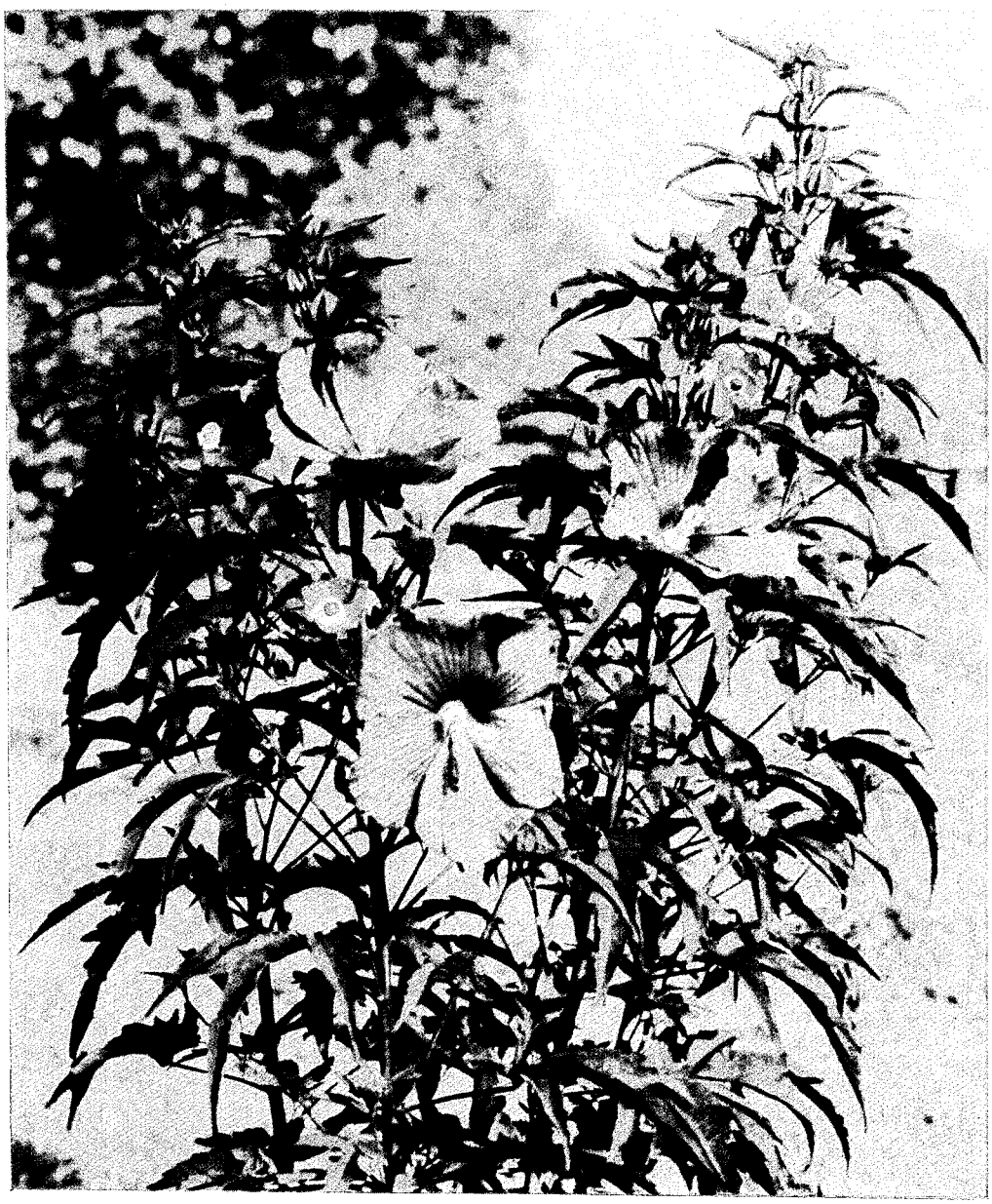
Inventor
Ernest Hemming
By: Robb & Robb
attorneys Patented May 10, 1949 Plant Pat. 835

UNITED STATES PATENT OFFICE

835

HYBRID MALLOW PLANT

Ernest Hemming, Easton, Md., assignor to Eastern Shore Nurseries, Inc., Easton, Md., a corporation of Maryland Application August 27, 1947, Serial No. 770,847

1 Claim. (Cl. 47—60)

The present invention relates to a new and distinct variety of mallow or hibiscus plant, resulting from a definite effort, over a period of time, to produce by hybridization and selections a plant variety eliminating certain undesirable coarse characters of known varieties and at the same time obtain a combination of desired features possessed by its antecedents. This objective has now been reached.

To be more specific, the hybridization was conducted over a series of years using as the three original parents, *Hibiscus militaris, Hibiscus coccinea,* and *Hibiscus moscheutos,* and selections were continuously made from the offspring of these various crosses.

The objective was primarily to develop a plant with the following characteristics, modified from the form in which they might occur in the parents by the combination make-up of the qualities in the new variety:

(*a*) Glabrous, deeply cut foliage, as distinguished from the coarse, hairy type found in the parent varieties.

(*b*) Deep, rich red color of flower, with petals opening flat, all overlapping and of sufficient hardiness to withstand the temperate zone.

It may be here noted that one of the original parents of this new variety, *Hibiscus coccinea,* is quite tender and while it has a red flower (not so dark as this new variety), the petals do not overlap and it is, therefore, quite unsatisfactory as a commercial product for this reason. Further, the parent *Hibiscus moscheutos* produces only white and pink flowers which are cup-shaped rather than flat in open form, so that this variety did not come up to requirements of the ideal plant.

In addition to these distinctions, the cross breeding and selection carried out was aimed to get rid of the large and coarse growing nature of the parent varieties. This object was also achieved and the present variety will be observed to be a medium sized plant with medium sized flowers of attractive form and color and possessing the other qualities and characters first referred to.

Asexual reproduction of this new variety shows the foregoing characteristics come true to form and are established.

The drawing shows specimen plant with flowers in various stages of opening of the blooms to the flat overlapping arrangement shown at approximately the center of the illustration.

The following is a detailed description of the new variety, color terminology being in accordance with Ridgway's Color Standard, except where otherwise indicated to have ordinary dictionary significance:

Type: Tender; shrub; herbaceous perennial.
Class: Hybrid, variety of hibiscus or mallow.
Breeding: Seedling—selected from crosses from three parents, *Hibiscus moscheutos, Hibiscus coccinea,* and *Hibiscus militaris* and subsequent progeny.

Propagation: Holds its distinguishing characteristics through succeeding propagations by cuttings and division (other methods not yet tried).
Leaves: Moderately abundant; moderately large; moderately heavy; glossy.
*Margins.*—Length six to eight inches; irregularly serrate. *Color*—dark green. Under side of leaves—medium green. New leaves—medium green and shiny.
*Petiole.*—Length—four to six inches. Lenticels—none.
*Leaf.*—Mostly 5-parted; palmately lobed. Central vein—reddish, not pubescent.
*Stipules.*—None.
Stem: Reddish with bloom.
Height: Medium—four to five feet.

*Flower*

Date described: July 23, 1947.
Petals: Length—three to four inches.
Diameter: Six to eight inches—overlapping.
Stamen tube: Color—red.
Filaments: Color—light red.
Stamens: Numerous.
Stigma: Color—red.
Style: Color—Carmine, Plate I.
Base of pistil or very center of throat: Color—white.
Pollen: Color—Light Orange Yellow, Plate III.
Shape of flower: Round.
Color of flower:
*Inside.*—Ox-Blood Red, Plate I, with quite a bit of Carmine, Plate I, veining through it, making it bright.
*Outside.*—Ox-Blood Red, Plate I, with veining Nopal Red, Plate I.
*In throat.*—A ring of Ox-Blood Red, Plate I, but deeper.
Flowers: Numerous; opening flat—not coarse or rank; individual flower lasting one day.
Blooming period: July, August, September, and occasionally to frost.
Peduncle: Length—four to six inches; medium thickness; stiff.
Stipules: none.

I claim:

A new and distinct variety of mallow plant, characterized as to novelty by its rich red color of flowers, of medium size, and opening flat with overlapping petals; its deeply cut, dark green and shiny foliage, lacking the usual coarseness and hairiness of other varieties; by the hardiness of the plant, its medium size habit of growth and reddish color of stem, substantially as shown and described.

ERNEST HEMMING.

No references cited.